(12) United States Patent
Skujins et al.

(10) Patent No.: US 8,137,292 B2
(45) Date of Patent: Mar. 20, 2012

(54) ELONGATED MEDICAL DEVICE FOR INTRACORPORAL USE

(75) Inventors: Peter Skujins, Minneapolis, MN (US); Brian R. Reynolds, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 162 days.

(21) Appl. No.: 11/769,569

(22) Filed: Jun. 27, 2007

(65) Prior Publication Data
US 2008/0015471 A1 Jan. 17, 2008

Related U.S. Application Data

(62) Division of application No. 10/729,076, filed on Dec. 5, 2003, now Pat. No. 7,237,313.

(51) Int. Cl.
- *A61B 5/00* (2006.01)
- *A61M 25/00* (2006.01)
- *A61F 11/00* (2006.01)
- *B25G 3/28* (2006.01)
- *E04B 1/49* (2006.01)
- *F16D 1/072* (2006.01)
- *B21C 47/26* (2006.01)
- *B21F 45/00* (2006.01)
- *B21F 15/02* (2006.01)

(52) U.S. Cl. ........... 600/585; 606/108; 140/2; 140/71 R; 140/111; 403/274; 403/280; 403/282

(58) Field of Classification Search .................. 600/585, 600/433, 434; 29/505, 517, 525.01, 525.13, 29/525.14; 140/2, 71 R, 111; 403/274, 280, 403/282; 604/264, 273, 423, 524, 525, 528, 604/533, 534, 538; 606/108
See application file for complete search history.

(56) References Cited

U.S. PATENT DOCUMENTS
2,132,575 A * 10/1938 Moise .................. 285/288.1
(Continued)

FOREIGN PATENT DOCUMENTS
EP 0 709 109 5/1996

*Primary Examiner* — Max Hindenburg
*Assistant Examiner* — John Pani
(74) *Attorney, Agent, or Firm* — Seager, Tufte & Wickhem, LLC

(57) ABSTRACT

Alternative designs, materials and manufacturing methods for medical devices. Some embodiments disclosed deal with attachment of an elongated structure, such as a wire or ribbon, or a tubular member, such as a coil, to an elongated member in an elongated device. For example, an elongated core member having defining an outer surface, and an elongated structure including a first portion and a second expanded portion along the length thereof can be provided. An attachment member, such as a centering ring, or the like, is disposed about a portion of the elongated core member and a part of the first portion of the elongated structure. The attachment member defines a lumen and having an inner surface. Part of the first portion of the elongated structure is disposed between the inner surface of the attachment member and the outer surface of the elongated core member. A part of the second portion of the elongated structure is in mechanical engagement with the inner surface of the attachment member and the outer surface the elongated core member to provide a mechanical coupling of the elongated structure between the attachment member and the elongated core member. Some embodiments provide a method of making such a construction, wherein the elongated structure can be moved relative to the attachment member such that the second portion of the elongated structure engages the inner surface of the attachment member and the outer surface the elongated core member to mechanically couple the elongated structure to the elongated core member.

24 Claims, 6 Drawing Sheets

U.S. PATENT DOCUMENTS

| | | | |
|---|---|---|---|
| 2,876,771 A * | 3/1959 | Dunmire | 604/141 |
| 3,174,851 A | 3/1965 | Buehler et al. | |
| 3,351,463 A | 11/1967 | Rozner et al. | |
| 3,749,086 A * | 7/1973 | Kline et al. | 600/585 |
| 3,753,700 A | 8/1973 | Harrison et al. | |
| 4,456,017 A | 6/1984 | Miles | |
| 4,538,622 A | 9/1985 | Samson et al. | |
| 4,619,274 A | 10/1986 | Morrison | |
| 4,832,047 A | 5/1989 | Sepetka et al. | |
| 4,886,067 A | 12/1989 | Palermo | |
| 4,966,163 A | 10/1990 | Kraus et al. | |
| 5,108,368 A | 4/1992 | Hammerslag et al. | |
| 5,238,004 A | 8/1993 | Sahatjian et al. | |
| 5,273,052 A | 12/1993 | Kraus et al. | |
| 5,275,173 A | 1/1994 | Samson et al. | |
| 5,365,944 A | 11/1994 | Gambale | |
| 5,372,144 A | 12/1994 | Mortier et al. | |
| 5,404,886 A | 4/1995 | Vance | |
| 5,409,015 A * | 4/1995 | Palermo | 600/585 |
| 5,415,178 A | 5/1995 | Hsi et al. | |
| 5,421,349 A | 6/1995 | Rodriguez et al. | |
| 5,488,959 A | 2/1996 | Ales | |
| 5,630,829 A * | 5/1997 | Lauterjung | 623/1.15 |
| 5,706,826 A | 1/1998 | Schwager | |
| 5,772,609 A | 6/1998 | Nguyen et al. | |
| 5,830,155 A | 11/1998 | Frechette et al. | |
| 5,865,768 A | 2/1999 | Orr | |
| 5,916,178 A * | 6/1999 | Noone et al. | 600/585 |
| 5,951,496 A | 9/1999 | Willi | |
| 5,957,865 A | 9/1999 | Backman et al. | |
| 5,980,471 A | 11/1999 | Jafari | |
| 6,132,388 A | 10/2000 | Fleming et al. | |
| 6,132,389 A | 10/2000 | Cornish et al. | |
| 6,139,510 A | 10/2000 | Palermo | |
| 6,159,165 A * | 12/2000 | Ferrera et al. | 600/585 |
| 6,387,060 B1 | 5/2002 | Jalisi | |
| 6,390,993 B1 | 5/2002 | Cornish et al. | |
| 6,475,167 B1 | 11/2002 | Fleming et al. | |
| 6,500,130 B2 | 12/2002 | Kinsella et al. | |
| 6,508,803 B1 | 1/2003 | Horikawa et al. | |
| 6,592,570 B2 | 7/2003 | Abrams et al. | |
| 6,602,208 B2 | 8/2003 | Jafari | |
| 6,645,159 B1 | 11/2003 | Burkett | |
| 6,702,762 B2 | 3/2004 | Jafari et al. | |
| 6,716,183 B2 | 4/2004 | Clayman et al. | |
| 6,740,050 B2 * | 5/2004 | D'Aquanni et al. | 600/585 |
| 6,799,067 B2 | 9/2004 | Pacetti | |
| 6,911,016 B2 | 6/2005 | Balzum et al. | |
| 6,918,882 B2 | 7/2005 | Skujins et al. | |
| 7,074,197 B2 | 7/2006 | Reynolds et al. | |
| 7,175,734 B2 | 2/2007 | Stewart et al. | |
| 7,182,735 B2 | 2/2007 | Shireman et al. | |
| 2003/0069521 A1 * | 4/2003 | Reynolds et al. | 600/585 |
| 2003/0120181 A1 | 6/2003 | Toma et al. | |
| 2004/0142643 A1 | 7/2004 | Miller et al. | |
| 2004/0167441 A1 | 8/2004 | Reynolds et al. | |

* cited by examiner

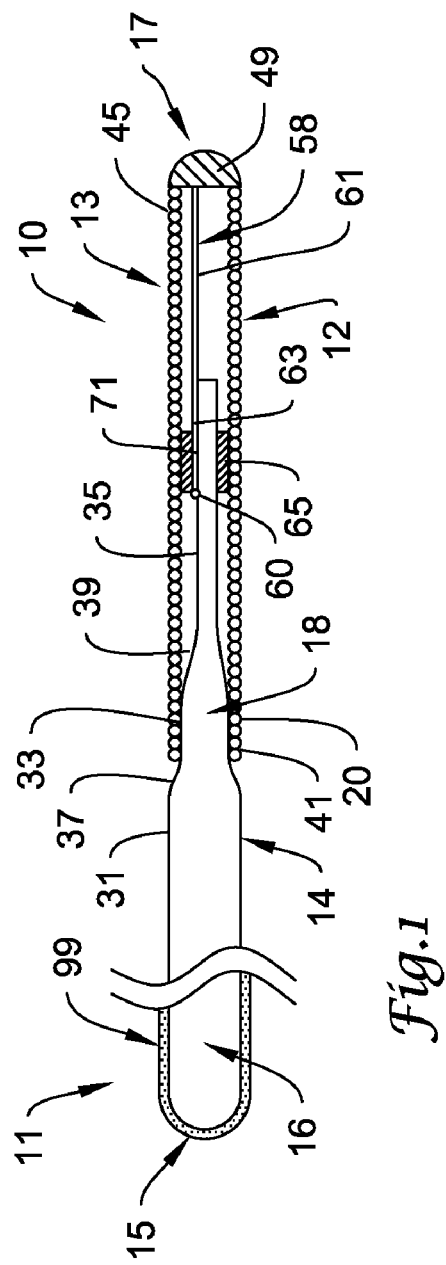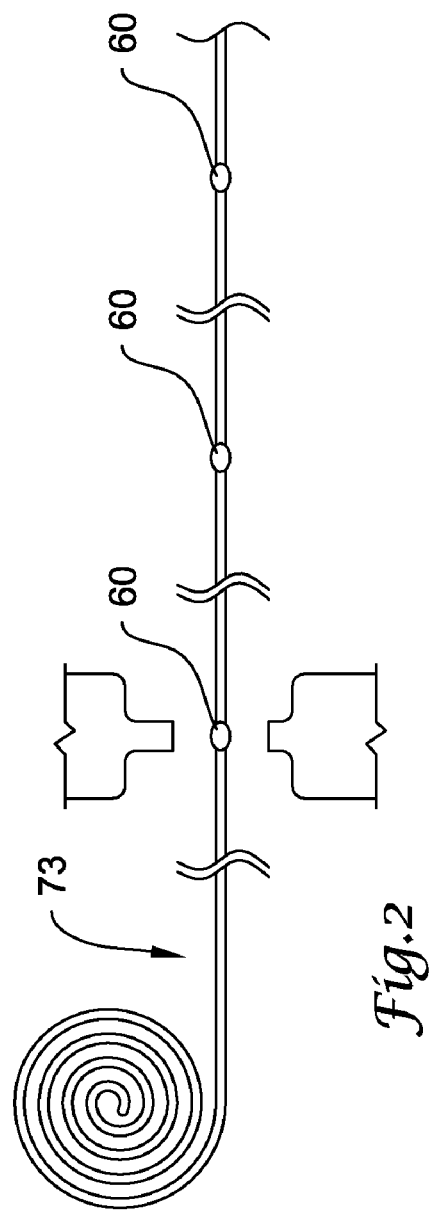

US 8,137,292 B2

ELONGATED MEDICAL DEVICE FOR INTRACORPORAL USE

RELATED APPLICATIONS

This application is a divisional of U.S. application Ser. No. 10/729,076, filed Dec. 5, 2003, now U.S. Pat. No. 7,237,313; all of which are incorporated herein by reference.

FIELD OF TECHNOLOGY

The invention generally pertains to intracorporal medical devices, such as guidewires, catheters, or the like.

BACKGROUND

A wide variety of medical devices have been developed for intracorporal use. Elongated medical devices are commonly used in to facilitate navigation through and/or treatment within the anatomy of a patient. Because the anatomy of a patient may be very tortuous, it is desirable to combine a number of performance features in such devices. For example, it is sometimes desirable that the device have a relatively high level of pushability and torqueability, particularly near its proximal end. It is also sometimes desirable that a device be relatively flexible, particularly near its distal end. A number of different elongated medical device structures and assemblies are known, each having certain advantages and disadvantages. However, there is an ongoing need to provide alternative elongated medical device structures and assemblies.

SUMMARY OF SOME EMBODIMENTS

The invention provides several alternative designs, materials and methods of manufacturing alternative elongated medical device structures and assemblies.

BRIEF DESCRIPTION OF THE DRAWINGS

The invention may be more completely understood in consideration of the following detailed description of various embodiments of the invention in connection with the accompanying drawings, in which:

FIG. 1 is a partial schematic cross sectional view of a guidewire in accordance with one example embodiment;

FIG. 2 is a partial schematic side view of a ribbon material being treated and/or worked to create expanded portions thereon;

Figure 3:
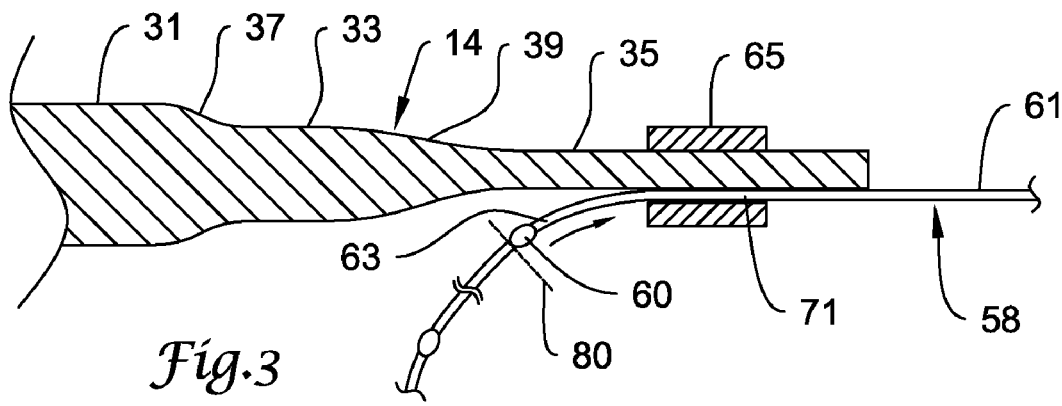
FIG. 3 is a partial schematic cross sectional view of a core wire for a guidewire, for example as shown in FIG. 1, showing a ribbon member being advanced into an attachment member at the distal portion of the core wire.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EXAMPLE EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. For example, although discussed with specific reference to guidewires in the particular embodiments described herein, the invention may be applicable to a variety of medical devices that are adapted to be advanced into the anatomy of a patient through an opening or lumen, and that can include a structure such as a ribbon or wire connected to another structure. For example, certain aspects of the invention may be applicable to fixed wire devices, catheters (e.g. balloon, stent delivery, etc.) drive shafts for rotational devices such as atherectomy catheters and IVUS catheters, endoscopic devices, laproscopic devices, embolic protection devices, spinal or cranial navigational or therapeutic devices, and other such devices. Many such devices may include a tip construction wherein a ribbon or wire is attached to the distal portion of a body or shaft member, and certain aspects of the invention disclosed herein may be useful in such constructions.

Some embodiments generally deal with attachment of an elongated structure, such as a wire or ribbon, or a tubular member, such as a coil, to a central member in an elongated device. At least some embodiments include an attachment member that can be disposed about the central member and define a space between the central member and the attachment member. A portion of the structure being coupled to the central member can be disposed within the space. The structure being connected can include an expanded or widened portion that is adapted and/or configured to mate with the attachment member and/or the central member when it is advanced toward the space defined there between.

For example some embodiments provide an elongated core member defining an outer surface, and an elongated structure including a first portion and a second expanded portion along the length thereof. An attachment member, such as a centering ring, or the like, is disposed about a portion of the elongated core member and a part of the first portion of the elongated structure. The attachment member defines a lumen having an inner surface. Part of the first portion of the elongated structure is disposed between the inner surface of the attachment member and the outer surface of the elongated core member. A part of the second portion of the elongated structure is in mechanical engagement with the inner surface of the attachment member and the outer surface the elongated core member to provide a mechanical coupling of the elongated structure between the attachment member and the elongated core member.

Some other embodiments provide a method of making such a construction. For example, the elongated core member and the elongated structure can be provided. An attachment member can be disposed about a portion of the elongated core member and the first portion of the elongated structure such that the first portion of the elongated structure is disposed between the inner surface of the attachment member and the outer surface of the elongated core member. The elongated structure can then be moved relative to the attachment member such that the second expanded portion of the elongated structure engages the inner surface of the attachment member and the outer surface the elongated core member to mechanically couple the elongated structure to the elongated core member.

Refer now to FIG. 1 which is a partial cross-sectional view of an example medical device 10. In at least some embodiments, device 10 may be a guidewire that, for example, includes proximal guidewire region 11 and a distal guidewire region 13. The proximal region 11 includes proximal end 15, and the distal region 13 includes a distal end 17. The guidewire 10 includes a core wire or member 14 including a proximal region 16 and a distal region 18. An outer structural member 12 is connected to the core member 14. In the embodiment shown, the outer structural member 12 is a coil member 12 connected to the core member 14 adjacent the distal region 13, however, alternative, and/or additional such structures are contemplated. Additionally, the guidewire includes an elongated distal structure 58 coupled to the distal region 18 of the core member 14, and an attachment member 65 disposed on and/or about a portion of the core member 14 and the distal structure 58. In the embodiment shown, the elongated distal structure 58 includes a ribbon and/or wire 58 that includes a widened and/or expanded portion 60 disposed thereon that can be adapted and/or configured to engage the attachment member 65 and/or the core member 14 and can be used in coupling the structure 58 to the core member 14, as will be discussed in more detail below.

Those of skill in the art and others will recognize that the materials, structure, and dimensions of the guidewire 10, and the components thereof, are dictated primary by the desired characteristics and function of the final guidewire 10. For example, the materials, structure, and dimensions of the core member 14, the coil member 12, the distal structure 58, the attachment structure 65, and any other components or structures used can vary widely, depending for example upon the desired characteristics and function of the final guidewire 10. Additionally, alternative constructions, for example tip constructions are also contemplated. For example, rather than including a coil member 12, the guidewire may include a polymer tip construction, or a combination of a polymer tip and a coiled tip, or other such constructions. Additionally, the guidewire may also include additional structures or assemblies, as desired, to achieve particular properties or characteristics. For example, the guidewire may include one or more radiopaque marker members, such as bands or coil, one or more additional coils or centering members, extension assemblies or structures, or the like, or other structures that can be incorporated into the construction of the device 10. Some example embodiments of materials, structure, dimensions and alternative constructions that may be used in guidewires are disclosed in U.S. Pat. Nos. 6,918,882, 7,074, 197, and 7,182,735; and U.S. Patent Publication No. 2004/0167441, all of which are incorporated herein by reference.

The core wire or member 14 includes a proximal region 16 and a distal region 18. Core member 14 can be made of any suitable materials including metals, metal alloys, polymers, elastomers, such as high performance polymers, or the like, or combinations or mixtures thereof. Some examples of suitable metals and metal alloys include stainless steel, such as 304V, 304L, and 316L stainless steel; nickel-titanium alloy, such as linear elastic or superelastic (i.e., pseudoelastic) nitinol; nickel-chromium alloy, nickel-chromium-iron alloy, cobalt alloy, tungsten, tungsten alloy, tantalum or tantalum alloys, gold or gold alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), Elgiloy, hastelloy; monel 400; inconel 625; or the like; or other suitable material, or combinations or alloys thereof.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties.

In some embodiments, a superelastic alloy, for example a superelastic nitinol can be used to achieve desired properties. Such alloys typically display a substantial "superelastic plateau" or "flag region" in its stress/strain curve. Such alloys can be desirable in some embodiments because a suitable superelastic alloy can provide a core member 14, or portion thereof, that exhibits some enhanced ability, relative to some other non-superelastic materials, of substantially recovering its shape without significant plastic deformation, upon the application and release of stress, for example, during insertion or navigation of the guidewire in the body.

In some other embodiments, a linear elastic alloy, for example a linear elastic nitinol can be used to achieve desired properties. For example, in some embodiments, certain linear elastic nitinol alloys can be generated by the application of cold work, directional stress, and heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C., and in other embodiments, in the range of about −100° C. to about 100° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows the core member 14 to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In at least some embodiments, portions or all of core member 14, or other structures of the guidewire 10, may be doped with, made of, coated or plated with, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility is imparted into the core member 14, or other portions of the device 10. For example, to enhance compatibility with Magnetic Resonance Imaging (MRI) machines, it may be desirable to make core member 14, or other portions of the medical device 10, in a manner that would impart a degree of MRI compatibility. For example, core member 14, or portions thereof, may be made of a material that does not substantially distort the image and create substantial artifacts (artifacts are gaps in the image). Certain ferromagnetic materials, for example, may not be suitable because they may create artifacts in an MRI image. Core member 14, or portions thereof, may also be made from a material that the MRI machine can image. Some materials that exhibit these characteristics include, for example, tungsten, Elgiloy, MP35N, nitinol, and the like, and others.

The entire core member 14 can be made of the same material, or in some embodiments, can include portions or sections made of different materials. In some embodiments, the material used to construct core member 14 is chosen to impart varying flexibility and stiffness characteristics to different portions of core member 14. For example, proximal region 16 and distal region 18 may be formed of different materials, for example materials having different moduli of elasticity, resulting in a difference in flexibility. In some embodiments, the material used to construct proximal region 16 can be relatively stiff for pushability and torqueability, and the material used to construct distal region 18 can be relatively flexible by comparison for better lateral trackability and steerability. For example, proximal region 16 can be formed of straightened 304v stainless steel wire or ribbon, and distal region 18 can be formed of a straightened super elastic or linear elastic alloy, for example a nickel-titanium alloy wire or ribbon.

In embodiments where different portions of core member 14 are made of different material, the different portions can be connected using any suitable connecting techniques. For example, the different portions of the core wire can be connected using welding (including laser welding), soldering, brazing, adhesive, or the like, or combinations thereof. Additionally, some embodiments can include one or more mechanical connectors or connector assemblies to connect the different portions of the core wire that are made of different materials. The connector may include any structure generally suitable for connecting portions of a guidewire. One example of a suitable structure includes a structure such as a hypotube or a coiled wire which has an inside diameter sized appropriately to receive and connect to the ends of the proximal portion and the distal portion. Some other examples of suitable techniques and structures that can be used to interconnect different shaft sections are disclosed in U.S. Pat. Nos. 6,918,882, 7,074,197 and 7,182,735; and U.S. Patent Publication No. 2004/0167441, all of which are incorporated herein by reference.

The length of core member 14 (and/or device 10), or the length of individual portions thereof, are typically dictated by the length and flexibility characteristics desired in the final medical device. For example, proximal region 16 may have a length in the range of about 20 to about 300 centimeters or more, distal region 18 may have a length in the range of about 3 to about 50 centimeters or more, and the guidewire 10 may have a total length in the range of about 25 to about 350 centimeters or more. It can be appreciated that alterations in the length of portions $^{16}/_{18}$ can be made without departing from the spirit of the invention.

Core member 14 can have a solid cross-section, but in some embodiments, can have a hollow cross-section. In yet other embodiments, core member 14 can include a combination of areas having solid cross-sections and hollow cross sections. Moreover, core 14, or portions thereof, can be made of rounded wire, flattened ribbon, or other such structures having various cross-sectional geometries. The cross-sectional geometries along the length of shaft 14 can also be constant or can vary. For example, FIG. 1 depicts core member 14 as having a round cross-sectional shape. It can be appreciated that other cross-sectional shapes or combinations of shapes may be utilized without departing from the spirit of the invention. For example, the cross-sectional shape of core member 14 may be oval, rectangular, square, polygonal, and the like, or any suitable shape.

As shown in FIG. 1, distal region 18 may include one or more tapers or tapered regions. In some embodiments distal region 18 may be tapered and have an initial outside size or diameter that can be substantially the same as the outside diameter of proximal region 16, which then tapers to a reduced size or diameter. For example, in some embodiments, distal region 18 can have an initial outside diameter that is in the range of about 0.010 to about 0.040 inches, that tapers to a diameter in the range of about 0.001 to about 0.005 inches. The tapered regions may be linearly tapered, tapered in a curvilinear fashion, uniformly tapered, non-uniformly tapered, or tapered in a step-wise fashion. The angle of any such tapers can vary, depending upon the desired flexibility characteristics. The length of the taper may be selected to obtain a more (longer length) or less (shorter length) gradual transition in stiffness.

In the embodiment shown in FIG. 1, the distal region 18 includes three constant diameter regions 31, 33, and 35, interconnected by two tapering regions 37 and 39. The constant diameter regions 31, 33, and 35 and tapering regions 37 and 39 are disposed such that the distal region 18 includes a geometry that decreases in cross sectional area toward the distal end thereof. In some embodiments, these constant diameter regions 31, 33, and 35 and tapering regions 37 and 39 are adapted and configured to obtain a transition in stiffness, and provide a desired flexibility characteristic. Also in some embodiments, portions of the distal region 18 can be flattened, for example, to provide for desired flexibility characteristics, or to provide an attachment area for other structure. For example, constant diameter portion 35 could include a portion thereof that is flattened.

Although FIG. 1 depicts distal region 18 of core member 14 as being tapered, it can be appreciated that essentially any portion of core member 14 may be tapered and the taper can be in either the proximal or the distal direction. As shown in FIG. 1, the tapered region may include one or more portions where the outside diameter is narrowing, for example, the tapering regions 37 and 39, and portions where the outside diameter remains essentially constant, for example, constant diameter regions 31, 33, and 35. The number, arrangement, size, and length of the narrowing and constant diameter portions can be varied to achieve the desired characteristics, such as flexibility and torque transmission characteristics. The narrowing and constant diameter portions as shown in FIG. 1 are not intended to be limiting, and alterations of this arrangement can be made without departing from the spirit of the invention.

The tapered and constant diameter portions of the tapered region may be formed by any one of a number of different techniques, for example, by centerless grinding methods, stamping methods, and the like. The centerless grinding technique may utilize an indexing system employing sensors (e.g., optical/reflective, magnetic) to avoid excessive grinding of the connection. In addition, the centerless grinding technique may utilize a CBN or diamond abrasive grinding wheel that is well shaped and dressed to avoid grabbing core wire during the grinding process. In some embodiments, core member 14 can be centerless ground using a Royal Master HI-AC centerless grinder. Some examples of suitable grinding methods are disclosed in U.S. Patent Publication No. 2004/0142643, which is herein incorporated by reference.

The coil member 12 is disposed about a portion of the distal region 18. It should be understood that in other embodiments, the member 12 may include other structures, such as a tubular sleeve or jacket, such as a polymer jacket. The coil member 12 may be made of a variety of materials including metals, metal alloys, polymers, and the like, including those described above with regard to the core member 14. In some embodiments, the coil member 12 can include multiple portions or layers wherein different portions or layers can include or be made of different materials. Additionally, the coil member 12 can be made of, coated or plated with, or otherwise include a radiopaque and/or can include materials or structure to impart a degree of MRI compatibility, as discussed above in relation to the core member 14.

The coil member 12 may be formed of round wire or flat ribbon ranging in dimensions to achieve the desired flexibility. It can also be appreciated that other cross-sectional shapes or combinations of shapes may be utilized without departing from the spirit of the invention. For example, the cross-sectional shape of wires or filaments used to make the coil may be oval, rectangular, square, triangle, polygonal, and the like, or any suitable shape. In some embodiments, the coil is made of rounded wire having a diameter of about 0.001 to about 0.004 inches.

The coil member 12 can be wrapped in a helical fashion by conventional winding techniques. The pitch of adjacent turns of coil member 12 may be tightly wrapped so that each turn touches the succeeding turn or the pitch may be set such that coil member 12 is wrapped in an open fashion. In some embodiments, the coil can have a pitch of up to about 0.05 inches, in some embodiments a pitch of up to about 0.02 inches, and in some embodiments, a pitch in the range of about 0.001 to about 0.004 inches. The pitch can be constant throughout the length of the coil member 12, or can vary, depending upon the desired characteristics, for example flexibility. These changes in coil pitch can be achieved during the initial winding of the wire, or can be achieved by manipulating the coil after winding or after attachment to the guidewire. Additionally, in some embodiments, portions or all of the coil member 12 can include coil windings that are pre-tensioned or pre-loaded during wrapping, such that each adjacent coil winding is biased against the other adjacent coil windings to form a tight wrap. Such preloading could be imparted over portions of, or over the entire length of the coil member 12.

The diameter of the coil member 12 is preferably sized to fit around and mate with a portion of the core member 14, and to give the desired characteristics. The diameter of the coil member 12 can be constant or tapered. In some embodiments, the coil member 12 is tapered, for example, to mate with a tapered section of the guidewire 10, or with other structure. The diameter of the coil member 12 can also include a taper beyond the distal end of the core member 14, as desired. In some example embodiments, the coil member 12 can have an outer diameter that is generally constant, and is in the range of about 0.01 to about 0.015 inches, and the inner diameter of the coil can also be generally constant, and is in the range of about 0.004 to about 0.013 inches.

The coil member 12 can be disposed about the core member in any of a broad variety of configurations. In the particular embodiment shown, the coil member 12 can extend about a portion of the distal section 18 from a point adjacent the tapering region 37 distally to a point distal of the distal most portion of the core member 14. The coil member 12 is attached to the distal core wire section 18 at its proximal end 41 at one or more attachment areas using a suitable attachment technique, including, for example, soldering, welding, heat crimping, adhesive, mechanical bonding or fitting, or combinations thereof, or the like. The distal end 45 of the coil member 12 can be attached to a tip portion, for example, a rounded tip portion 49. The rounded tip portion 49 can be made of any suitable material, for example a solder tip, a polymer tip, a metal and/or metal alloy tip, or combinations thereof, or the like. Attachment to the tip portion 49 can be made using any suitable technique, including, for example, soldering, welding, heat crimping, adhesive, mechanical bonding or fitting, or combinations thereof, or the like. It should be understood, however, that these attachment areas are given by way of example only, and that the coil member 12 can be attached at different locations and by using more or fewer attachment areas, as desired, without parting from the spirit and scope of the invention.

For example, in some other embodiments, portions of the coil member 12 may be attached to other structure, for example, a spacer member, a centering ring (such as structure 65), an additional coil, a shaping or safety ribbon or wire, or may be free of attachment. Additionally, the coil member 12 can be attached to the core member 14 or other structure at one or more intermediate areas. Additionally, in other embodiments, the coil member 12 can be disposed at other locations along the length of the guidewire 10, or could extend the entire length of the guidewire 10. In some embodiments, the coil member 12 can be in the range of about 1 to about 20 inches long.

The embodiment of FIG. 1 shows an attachment member 65, that is disposed about the distal section 18, and a portion of the elongated distal structure 58 is disposed between the attachment member 65 and the distal section 18. The attachment member 65 can include a broad variety of structures, for example a member such as a hypotube, a coiled member, a clip, a band, a ring, or the like, or other structures, and may be non-coiled as shown in FIGS. 1 and 3-5. The attachment member 65 can be adapted and/or configured to include a lumen, opening, or notch therein in which a portion of the core member may extend. The attachment member 65 can be adapted to be disposed about at least a portion of the core member 14 such that a space or gap 71 can be created between the inner surface of the attachment member and the outer surface of the core wire, wherein a portion of the elongated distal structure 58 may extend. In some embodiments, for example, in FIG. 1, the attachment member can be a generally tubular centering ring 65 that is adapted or configured to fit over a portion of the distal section 16, and in at least some embodiments, is adapted or configured to engage and/or attach to the elongated distal structure 58 and the distal section 16. Additionally, the centering ring 65 can also be adapted and/or configured to engage, or be attached to an outer member, such as a coil member 12, to provide a supporting or centering function for the coil member 12, or may be free of any engagement or attachment to the coil member 12. If attached, the coil member 12 may be attached to the centering ring 65, using any suitable attachment technique, for example soldering, brazing, welding, adhesive bonding, heat crimping, mechanical crimping, or the like.

The centering ring 65 may be made of a variety of materials including metals, metal alloys, polymers, and the like, including those described above with regard to the core member 14. In some embodiments, the centering ring 65 can include multiple portions or layers wherein different portions or layers can include or be made of different materials. Additionally, the centering ring 65 can be made of, coated or plated with, or otherwise include a radiopaque material and/or can include materials or structure to impart a degree of MRI compatibility, as discussed above in relation to the core member 14.

The dimensions of the centering ring 65 can vary greatly, but the centering ring is preferably sized to fit around and mate with a portion of the core member 14 and ribbon 58, and to give the desired characteristics. The outer and/or inner diameters of the centering ring 65 can be constant or tapered. In some embodiments, the centering ring 65 is tapered, for example, to mate with a tapered section of the guidewire 10, or with other structure. In some example embodiments, the centering ring 65 can have an outer diameter that is generally constant, and is in the range of about 0.005 to about 0.03 inches, and the inner diameter of the centering ring 65 can also be generally constant, and is in the range of about 0.004 to about 0.025 inches. The length (along the longitudinal axis of the guidewire) of the centering ring 65 can also vary, depending upon the desired characteristics, but in some embodiments can be in the range of about 0.015 to about 0.25 inches.

The centering ring 65 can be disposed about the core member 14 in any of a broad variety of configurations. In the particular embodiment shown, the centering ring 65 can extend about a portion of the distal section 18. It should be understood, however, that this configuration is given by way of example only, and that the centering ring 65 can be disposed at different locations, as desired, without parting from the spirit and scope of the invention.

The elongated distal structure 58 coupled to the distal region 18 of the core member 14, may include a ribbon, wire, filament, or other such structure. In the embodiment of FIG. 1, the structure 58 is shown as a generally straight ribbon, but it should be understood that other configurations may be used. For example the ribbon could be worked, curved, and/or shaped such that it includes one or more curves, bends, twists, or the like along the length thereof. In some other embodiments, the structure 58 may include a portion that is coiled, or tubular shaped. The ribbon 58 can be an elongated structure having a longitudinal axis, and having a distal region 61 and a proximal region 63. The ribbon includes an outer surface including an outer perimeter. The ribbon 58 is coupled to the core member 14 adjacent the distal section 16, and extends distally of the distal end of the core wire. In the embodiment shown, the ribbon 58 is a generally straight ribbon that overlaps with and is coupled to the distal section 16.

The ribbon 58 includes a widened and/or expanded region or portion 60. In the embodiment shown the expanded portion 60 is disposed adjacent the proximal region 63 of the ribbon 58, however, in other embodiments, the widened portion 60 can be disposed at other locations along the length of the ribbon 58. The expanded portion 60 can be a portion of the ribbon 58 that includes at least one dimension along the outer perimeter thereof that is greater than the same dimension of other portions of the ribbon 58. For example, the expanded portion 60 may include a width, thickness, height, diameter, radius, or other such dimension that is greater than the same dimension of an adjacent portion of the ribbon 58. In another respect, the expanded or widened portion 60 of the ribbon 58 can include at least a part thereof that includes an outer surface that extends a further distance away from the central longitudinal axis of the ribbon 58 than an adjacent portion of the ribbon 58. For example, the widened portion 60 may include a dimple, a bifurcation, one or more twists, a widening, a head, or additional material or structure added thereto that created a dimensional change in the outer surface of the ribbon 58. As such, another portion of the ribbon 58, such as the distal region 61, may have an outer perimeter that is adapted and/or configured to fit within or extend through a space of predetermined size and shape, for example space 71, while the widened and/or expanded portion 60 of the ribbon 58 can be adapted and/or configured such that it cannot fit within or extend through the same space. The widened portion can be adapted and/or configured to engage the attachment member 65 and/or the core member 14 and can be used in coupling the ribbon 58 to the core member 14, as will be discussed in more detail below.

The ribbon 58 can be made of any suitable material and sized appropriately to give the desired characteristics, such as strength, torquability, and flexibility characteristics. Some examples of suitable materials include metals, metal alloys, polymers, and the like, and may include radiopaque materials or include materials or structure to impart a degree of MRI compatibility, as discussed above in relation to the core member 14 and coil member 12.

The following examples of some dimensions are included by way of example only, and are not intended to be limiting. In some embodiments, the ribbon 58 is a flattened ribbon having a width in the range of about 0.002 to about 0.008 inches, a thickness in the rang of about 0.0005 to about 0.003 inches, and a length in the range of about 0.25 to about 3.0 inches. The widened portion 60 of the ribbon 58 may include at least one dimension, such as width or thickness, that is greater than the remainder of the ribbon. For example, the widened portion 60 may have a width in the range of about 0.003 to about 0.2 inches, a thickness in the range of about 0.0005 to about 0.2 inches, and a length in the range of about 0.01 to about 0.25 inches. In some embodiments, the ribbon 58 overlaps with the distal section 18 by a length in the range of about 0.25 to about 2 inches, and includes a distal portion 61 that extends distally beyond the distal section 16 by a length in the range of about 0.1 to about 2.0 inches. The distal end of the ribbon 58 can be attached to other structure, such as the rounded tip portion 49, or may remain unattached. Attachment to the tip portion 49 can be made using any suitable technique, including, for example, soldering, welding, heat crimping, adhesive, mechanical bonding or fitting, or combinations thereof, or the like.

The expanded or widened portion 60 can be created in the ribbon in a broad variety of ways. For example, a ribbon structure can be initially created including widened portions 60 that are simply portions of the ribbon material that have additional material or include structures to provide a widened portion 60 in the dimensions of the ribbon material. Additionally, after the ribbon structure is initially created, a portion of the ribbon structure can be forged, stamped, dimpled, bifurcated, twisted, crimped, bent, or otherwise shaped to provide the desired dimensional change to create the widened portion 60. Furthermore, after the ribbon structure is initially created, additional material can be added, for example, through soldering, welding, adhesive bonding, or the like, to provide the desired dimensional change to create the widened portion 60.

For example, refer to FIG. 2, which shows one example embodiment of creating widened portions 60 in ribbon material 73. In this embodiment, an elongated section of ribbon material 73 has been provided in the form of an elongated section of ribbon in a coil. The coil of ribbon material 73 can be systematically treated or worked to create a plurality of widened or expanded portions 60 at predetermined intervals along the length of the ribbon material 73, for example through the use of a forging tool 50, or the like, or other mechanism for creating widened portions 60. In some cases, the widened portions can be created in the ribbon material 73 at predetermined length or spacing that correspond generally to the desired length of individual ribbons 58. After a widened portion 60 is created, the ribbon material 73 can be advanced relative to the forging tool 50 a desired distance, and an additional widened portion 60 can be created, and so fourth. Alternatively, the forging tool can be moved relative to the ribbon material. Thereafter, the ribbon material 73 may be cut at desired points to form individual ribbons 58 having a generally desired length, and including widened portions 60 disposed at a desired location along the length of each. Alternatively, the ribbon material 73 can remain intact, and can be cut during and/or after coupling of the ribbon 58 to the core member 14.

Figure 4:
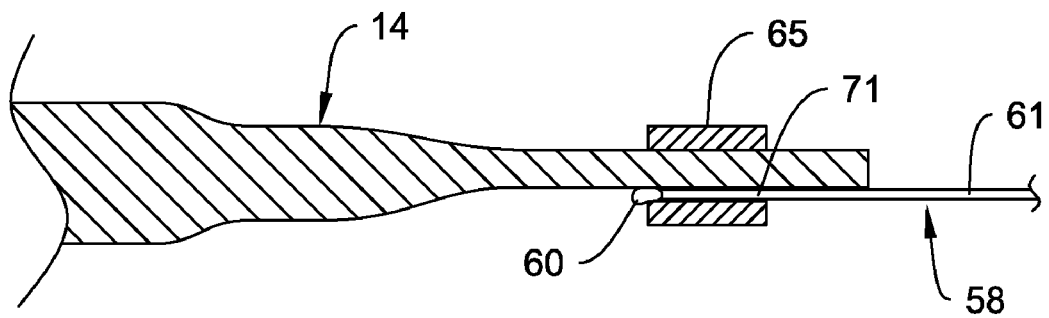
FIG. 4 is a partial schematic cross sectional view similar to that shown in FIG. 3, wherein the ribbon has been advanced such that an expanded portion thereon is in contact with the attachment member.

Refer now to FIGS. 3 and 4, which show one example embodiment of coupling the ribbon 58 to the core member 14. Referring to FIG. 3, a portion of the ribbon member is disposed within the lumen of the centering ring 65, and the centering ring 65 is disposed at a desired location about a portion of the core member 14. A space or gap 71 is formed between the inner surface of the centering ring 65 and the outer surface of the core member 14 wherein the ribbon 58 is disposed. The distal region 61 of the ribbon member 58 can be slid, pulled, or otherwise disposed such that it extends within the space 71. The widened portion 60 of the ribbon 58 may remain proximal of the attachment member 65 during initial positioning. The ribbon member 58 can then be slid, pulled, or otherwise moved in a distal direction, such that the widened portion 60 is moved toward the attachment member 65.

In some embodiments, the ribbon 58 can be precut into a generally desired length prior to disposal into the space 71. In other embodiments, however, the proximal end of the ribbon 58 may remain connected to a length of ribbon material, for example ribbon material 73, during initial positioning, and can thereafter be cut to the desired length either during or after advancement of the widened portion 60 toward the attachment member 65. Such embodiments can be useful in construction of multiple guidewire structures in that a single length of ribbon material, for example ribbon material 73, can be used in the construction of multiple guidewire structures. The ribbon material 73 can be provided with multiple widened portions 60 as discussed above with reference to FIG. 2, and the distal end of the ribbon material 73 can be advanced within the space 71 of a first wire, and can thereafter be cut to the desired length either during or after advancement of the widened portion 60 toward the attachment member 65, for example at cut point 80. A new distal portion of the ribbon material 73 is thereby created by the cutting, and can thereafter be advanced within the space 71 of a second wire, and the procedure can be repeated. Such a sequence can be repeated for a plurality of guidewire constructions. Such an arrangement can be helpful, for example, in the efficiency and ease of manufacturing such guidewire assemblies.

Refer now to FIG. 4, wherein the widened portion 60 has been advanced into contact with the attachment member 65. Due to the dimensional difference of the widened portion as compared to the space 71, the widened portion 60 cannot slide through the space 71, and therefore engages the attachment member 65. The widened portion 60 mechanically engages, for example frictionally and/or interlockingly engages, the centering ring 65 and/or core member 14, and can create a mechanical coupling or bond between the centering ring 65, the ribbon 58, and/or the core member 14 such that the three components can remain in a static position relative to one another. In some embodiments, a portion of the widened portion 60 engages, and can provide a mechanical fit between the inner surface of the attachment member 65 and the outer surface of the core member 14. For example, the ribbon 58 can be advanced distally with a necessary amount of force to create a frictional and/or an interlocking fit of a part of the widened portion 60 between the attachment member 65 and the core member 14. In some embodiments, a part of the widened portion 60 may be deformed such that it fits tightly within the space 71 between the inner surface of the attachment member 65 and the outer surface of the core member 14.

In some embodiments, during initial positioning and/or the advancement of the widened portion 60 to achieve the coupling, a fixture may be used to aid in maintaining the relative position of the components. Any of a broad variety of fixtures may be used, or no fixture may be used, as will be appreciated by those of skill in the art and others. One example of a fixture 90 that may be used is shown in FIGS. 6 and 7.

Figure 6:
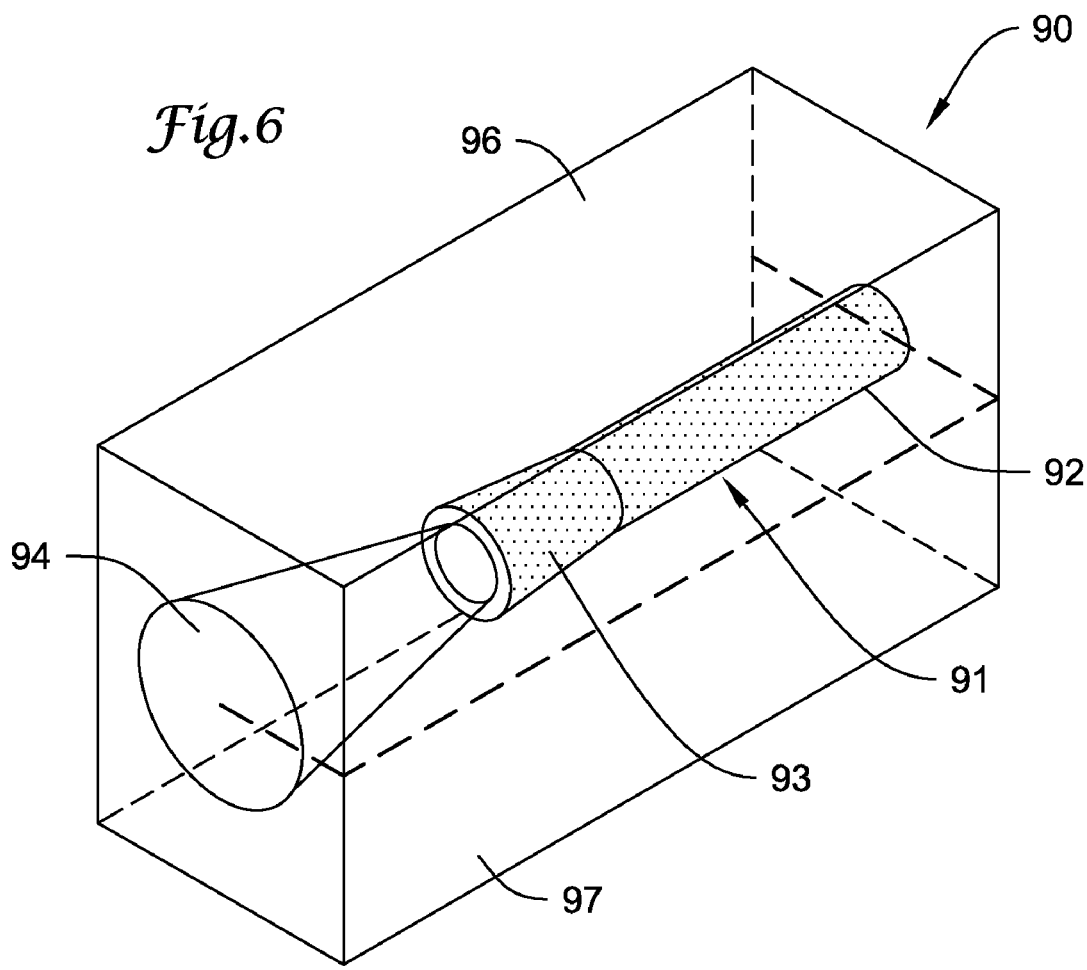
FIG. 6 is a partial schematic perspective view of a fixture that may be used in some embodiments.

Referring to FIG. 6, the fixture 90 may include two parts that when put together define a lumen 91 that is adapted and/or configured to maintain the desired relative positions of the attachment member 65, core member 14, and ribbon 58. The lumen 91 includes a first portion 92, a second portion 93, and a third portion 94. The first portion is adapted and/or configured to accept a portion of the core member 14 and ribbon 58, which may be advanced therein. The second portion 93 is adapted to accept the centering ring 65, and maintain the centering ring 65 at a desired position relative to the core member 14 and the ribbon. The third portion 94 is tapered outwardly, in a funnel like shape, and is adapted and/or configured such that the core member 14, ribbon 58, and/or the centering ring 65 may be advanced to desired positions within the fixture 90.

Figure 7:
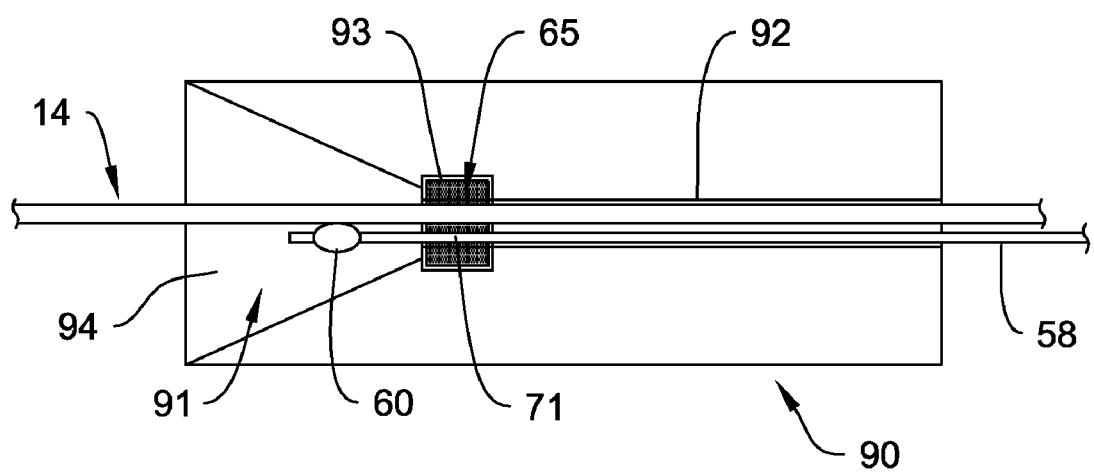
FIG. 7 is a top view of a bottom portion of the fixture shown in FIG. 6.

For example, FIG. 7 shows a top view of the bottom half of the fixture 90 including the attachment member 65, core member 14, and ribbon 58 disposed therein. The centering ring 65 is disposed in the second portion 93 of the lumen 91. The core member 14 can be introduced into the lumen through the third portion 94 and may be moved laterally such that the centering ring 65 is disposed about the core member 14 at a desired location along the length of the core member 14. The ribbon 58 can also be introduced into the lumen 91 through the third portion 94, and the ribbon 58 can thereafter be advanced distally such that the widened portion 60 is advanced toward the attachment member 65, for example, to create the mechanical bond between the three components, as discussed above in reference to FIGS. 3 and 4. The fixture 90 may aid in maintaining the relative position of the centering ring 65 on the core member 14 and/or ribbon as the coupling is achieved. Additionally, the fixture 90 may aid in allowing the application of sufficient force to deform and pull a part of the widened portion 60 of the ribbon 58 into the space 71 to form the coupling.

As disclosed above, a mechanical coupling or bond is created between the centering ring 65, the ribbon 58, and/or the core member 14 which can thereafter be further worked and/or incorporated into guidewire structure. In some embodiments, the coupling may be used as is, or in other embodiments, an additional attachment technique can thereafter be used to further connect one or more of the components together or to other structure.

In some embodiments, the creation of such a mechanical coupling or bond using such methods or techniques may have certain advantages. For example, in some embodiments, such a mechanical coupling or bond can aid in ensuring that there is a snug fit between the components. For example, without the use the mechanical coupling or bond discussed above, it can be difficult to ensure that there is a snug fit between the parts to provide for a good bond using other attachment techniques. For example, if there is too much space between the ribbon 58 and the core member 14, it may be difficult to achieve a good bond using additional attachment techniques such as a weld, braze, solder, crimp, adhesive, or other type of bond. However, the use of the widened portion 60 on the ribbon 58, as disclosed herein, ensures that there will be a snug fit, and may provide for a better bond.

Additionally, the use of the mechanical coupling or bond as disclosed herein can aid in maintaining relative positioning of the components, such as the ribbon 58, centering ring 65 and the core member 14, until or while other bonding techniques can be used to further couple the members together. For example, the mechanical coupling as disclosed herein can help prevent movement of the relative positioning of the members if the parts are rotated, bumped, or need to be otherwise moved. For example, if the assemblies are moved to another work station for the application of another attachment technique, the mechanical coupling will aid in maintaining the components in the desired positions relative to one another. The mechanical coupling can also aid in maintaining the relative positioning of the components while additional attachment techniques are applied. For example, when the ribbon 58, the centering ring 65 and the core member 14 are coupled together as disclosed above, the parts are less likely to jump or migrate as a result of solder float, flux outgassing, spattering, outflow from adhesives, or the like, that may occur while other attachment techniques are being applied.

Additionally, the mechanical coupling or bond can reduce the need to use other fixtures while applying additional attachment techniques. For example, fixtures are often necessary to maintain parts in position while other attachment techniques are used, such as welding, etc. Some attachment techniques, however, are not suitable for using complex holding fixtures. For example, welding, soldering, and brazing frequently require heating or focusing mechanisms that may be incompatible with precision location fixtures. Problems may be caused by stray heating, spattering, flux residue, and fixture damage from failed sequences. In some embodiments of the invention, however, such complex fixtures may not be necessary because the parts are held in relative position due to the mechanical coupling or bond created there between. For example, simple fixtures adapted and/or configured to maintain the mechanically coupled or bonded structures adjacent an appropriate attachment tool or system are all that may be required.

These and other possible benefits and/or advantages may be present in some embodiments, as will be recognized by those of skill in the art, and others, but are not requirements of all embodiments of the invention.

As indicated above, an additional attachment technique can be used to enhance the mechanical coupling or bond, or to further connect the components. Some examples of suitable attachment techniques include welding (e.g., resistance, TIG, friction, plasma, LASER, electron beam, or the like), soldered (e.g. radiant heat, LASER diode, or the like), brazing, the use of an expandable alloy (e.g. an expandable bismuth alloy, or the like), adhesive bonding, crimping, or the like, or other suitable technique, depending somewhat upon the material selected for each component, and the desired connection characteristics. Some examples of methods, techniques and structures that can be used to interconnect different portions of a guidewire are disclosed in U.S. Pat. Nos. 6,918,882, 7,074,197 and 7,182,735;and U.S. Patent Publication No. 2004/0167441, all of which are incorporated herein by reference.

Figure 5:
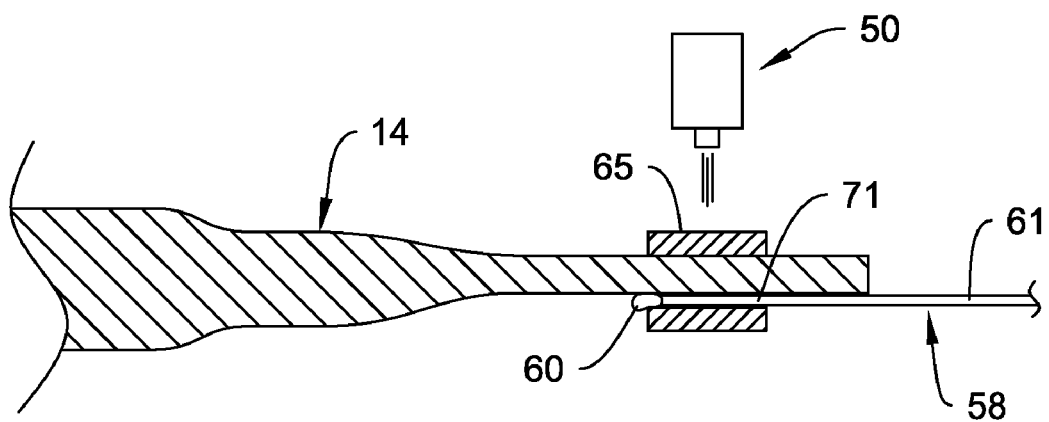
FIG. 5 is a partial schematic cross sectional view similar to that shown in FIG. 4, wherein the ribbon and attachment member can be further connected to each other and/or to the core member using a suitable attachment technique.

Refer now to FIG. 5, which shows an example of the use of an additional attachment technique to enhance the mechanical coupling or bond and/or to further connect one or more of the ribbon 58, the core wire 14, and/or the centering ring 65 to each other. FIG. 5 shows a connection tool or assembly 50, such as a solder tool, brazing tool, welding tool, or the like, disposed adjacent the centering ring 65. Such a tool or assembly can provide energy to portions of the centering ring 65, ribbon 58, and/or the core wire 14 to heat the material thereof to form a welded construction. Alternatively, a solder or brazing material could be applied to (either prior to, or during heating) one or more of the centering ring 65, ribbon 58, and/or the core wire 14, and the tool or assembly could be used to provide the heat necessary to activate the soldering or brazing material to form a soldered of brazed construction. In some embodiments, due to the mechanical coupling or bond that is already present, the amount of solder or brazing material that needs to be used to create a suitable joint may be reduced.

In some embodiments, prior to the application of such attachment techniques, a heat activated bonding or filler material, such as solder or brazing material, can be disposed adjacent to the centering ring 65. For example, the heat activated bonding or filler material could be used to form the widened portion 60 on the ribbon 58, which could be used to create the initial mechanical coupling or bond, and thereafter also be used for the additional attachment. Additionally, and/or alternatively, solder or brazing material can be disposed about the proximal end of the centering ring 65, adjacent to the lumen. It should be understood however, that in other embodiments, the solder or brazing material can be disposed or located at a different location, for example, adjacent the distal side of the centering ring 65, or alternatively, could be disposed in the desired attachment positions between the members to be connected prior to connection. The solder or brazing material could then be heated using an appropriate heat source, and will begin to flow into an attachment position between the ribbon 58 and the distal section 16, and/or between the ribbon 58 and the centering ring 65, and/or between the distal section 16 and the centering ring 65, or all of the above positions. Some examples of suitable heat sources for use in soldering or brazing are described above. However, in some embodiments, LASER energy is used as the heat source to provide for accuracy of heating, and to avoid undesirable heating of structures adjacent the attachment points.

It should be understood, however, that any of a broad variety of other suitable attachment techniques may be used that may not require such a connection tool or assembly 50, or may use a different connection tool or assembly. For example, due to the mechanical coupling or bond that is created between the centering ring 65, the ribbon 58, and/or the core member 14, other options for additional attachment technique can be used. For example, a number of assemblies (e.g. a number of the centering ring 65-ribbon 58-core member 14 assemblies) could be bulk processed by immersion in molten solder in a system such as a wave solder system, which may eliminate the need for pre-tinning operations and steps that may be needed to position additional filler material of solder material on the assembly. Additionally, heat could be induced in the assembly to achieve the desired connection by induction and/or ultrasonics, as well as by the more conventional radiation and/or conduction.

In some embodiments, the structures being connected can be pre-treated and/or pre-coated with a suitable attachment material prior to attachment, but this is not necessary in all embodiments. For example, the ribbon 58, or portions thereof, the distal section 16, or portions thereof, and/or the centering ring 65, or portions thereof, or all three, can be cleaned or treated to remove impurities or oxides. This can be useful, especially when any of the structures being connected includes materials that may be difficult material to weld, solder or braze, such as some nickel titanium alloys. Some examples of such treatments include acid baths or washes, fluxing, pickling, pre-tinning, pre-plating (i.e. plating with another material) and the like. In some embodiments, one or more of the surfaces of the structures to be connected can be cleaned and pre-plated with another metallic material, for example, a nickel plating. In some embodiments, the surface to be soldered or brazed is treated with a molten alkali metal hydroxide, and then pre-treated, or "pre-tinned" with a suitable solder or brazing material. It should also be understood within the context of this disclosure that when a heat activated attachment material, such as solder or brazing material, is used to connect two or more components, such heat activated attachment material can be predisposed on the components being connected using such processes or treatments, or can be separately disposed or added to make the connection. Therefore, the heat activated attachment material used for making such connections can come form either source ("pre-tinned" or "added"), or from both sources. The heat activated attachment material can include any suitable solder or brazing material, or the like. Some examples of suitable solder or brazing material include, but are not limited to, tin based materials, for example, gold-tin solder, silver-tin solder, and the like, and many others.

Additionally, in some embodiments, a cold bonding material, such as a high indium type solder, can be employed as a coating on one or more of the components, or may be used to form the widened portion 60 on the ribbon. Such materials have the ability to create a cold weld and/or solder that may be used to permanently lock or bond the components into the desired position after the initial mechanical coupling and/or bond is achieved without the use of additional treatment.

Furthermore, in some embodiments, the centering ring 65 may be adapted and/or configured for providing an additional attachment or bonding function. For example, the centering ring may include or be made of a shape memory material, such as a shape memory nitinol. In such embodiments, the shape memory effect can be used in the attachment of the centering ring 65 about the core wire 14 and/or the ribbon 58, for example, in causing compression of the centering ring 65 from a first expanded configuration to a second compressed configuration.

For example, in some embodiments, the centering ring can include or be made of a shape memory alloy that is martensite at temperatures significantly below room temperature, and has a final austenite transition temperature ($A_f$) somewhere slightly below, at, or above room temperature. In some such embodiments, it may be desirable that the final austenite transition temperature be at least slightly below room temperature, to ensure final transition at room temperature. For example, in some such embodiments, the shape memory alloy has a final austenite transition temperature in the range of about −10° C. and about 20° C. This feature allows the centering ring 65 to be disposed about the core wire 14 and/or the ribbon 58 while in a martensitic state at temperatures colder than the transition temperature. A mechanical coupling or bond could be achieved, for example as discussed above, between a widened portion 60 on the ribbon 58 and the centering ring 65 and core wire 14 while the centering ring 65 is in the martensitic state. The centering ring 65 can then be allowed to warm above the transition temperature and assume its preformed, compressed austenitic shape. As the centering ring 65 assumes the second compressed configuration, it causes a compressive force to be applied about the core wire 14 and/or the ribbon 58 and forms a bond to maintain the structures in position. Some examples or Nitinol cylindrical tubes having desired transition temperatures, as noted above, can be prepared according to known methods.

Additionally, a portion of the centering ring 65 may be mechanically crimped to achieve an additional locking force. While in some embodiments, the size and fragility of the centering ring 65 may preclude the use of such crimping as the sole mechanism for attaching mechanism for the assembly, it may be used in combination with other locking mechanisms, such as the mechanical coupling or bond formed using the widened portion 60 of the ribbon 58. For example, in some embodiments, the distal portion of the centering ring 65 may be crimped after the mechanical coupling or bond formed using the widened portion 60 of the ribbon 58.

After being coupled to the core wire 14, the ribbon 58 could be further worked and/or manipulated to achieve desired structures, and/or properties. For example, the distal portion of the ribbon 58 may be bent, shaped, twisted, coiled, and/or otherwise provided with a desired configuration. Additionally, the distal portion of the ribbon can be attached to other structure in the guidewire using suitable attachment techniques, or may be provided with an atraumatic distal tip, for example, by connection to the tip 49, such as solder tip, or other such structure. Alternatively, the distal portion of the ribbon may be heated and/or otherwise formed into a bulbous and/or atraumatic end.

Figure 8:
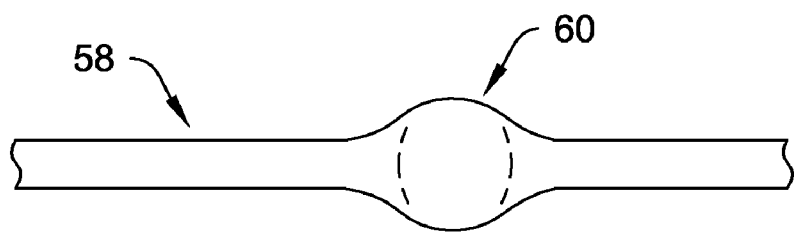
FIGS. 8-17 show views of some examples of different configurations that can be used for an expanded portion in the ribbon.
Figure 9:
Figure 10:
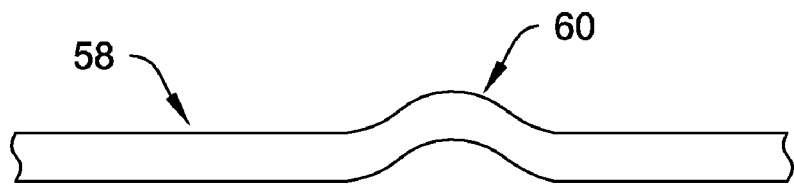
Figure 11:
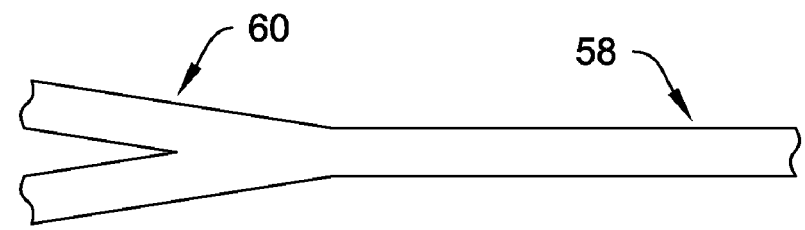
Figure 12:
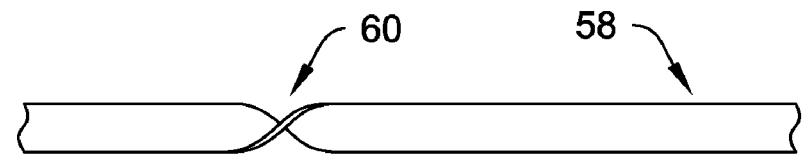
Figure 13:
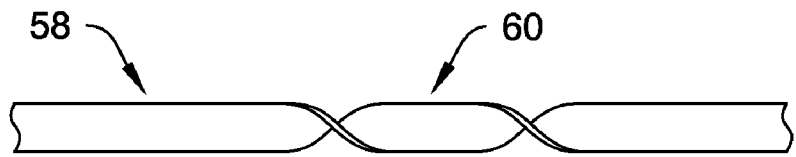
Figure 14:
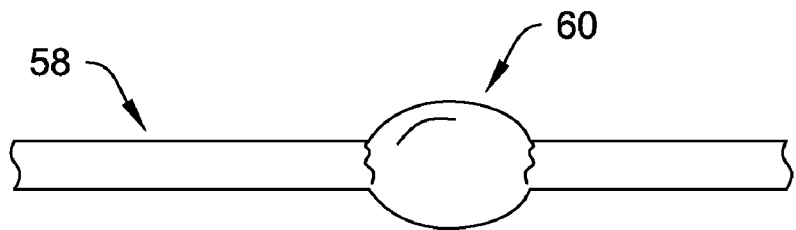
Figure 15:
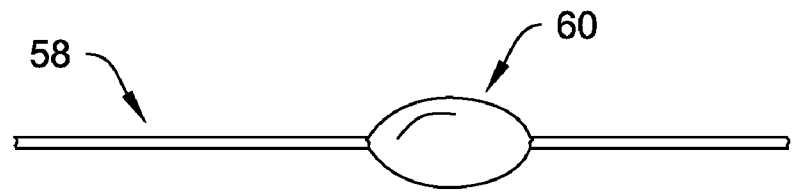
Figure 16:
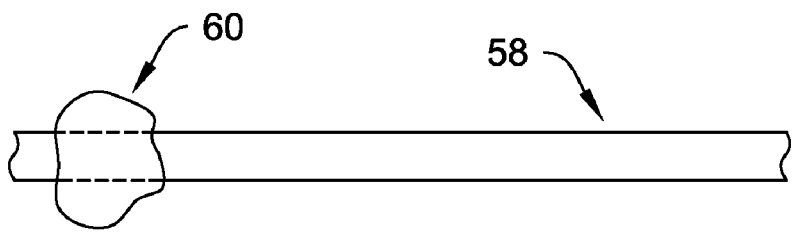
Figure 17:
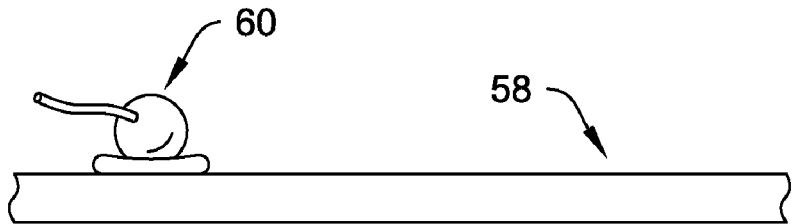

Refer now to FIGS. 8-17, which illustrate a number of example embodiments of expanded portions 60 that can be formed on the ribbon 58. FIG. 8 shows an example of a ribbon 58 including an expanded portion that can be formed, for example, through a forging procedure, which creates an increase in the width of the ribbon 58. FIG. 9 shows an example of a ribbon 58 including an expanded portion 60 that can be formed, for example, by creating a curved bend or "dimple" along the thickness of the ribbon 58. FIG. 10 shows an example of a ribbon 58 including a expanded portion that can be formed, for example, by creating a curved bend or "dimple" along the width of the ribbon 58. FIG. 11 shows an example of a ribbon 58 including an expanded portion that is formed, for example, by bifurcation of the ribbon 58. FIG. 12 shows an example of a ribbon 58 including an expanded portion that is formed, for example, by a twist in the ribbon 58. FIG. 13 shows an example of a ribbon 58 including an expanded portion that is formed, for example, by a double twist in the ribbon 58. FIG. 14 shows an example of a ribbon 58 including an expanded portion that is formed, for example, by the application of a cold bonding material, such as a high indium type solder, to increase the width of the ribbon 58. FIG. 15 shows an example of a ribbon 58 including an expanded portion that is formed, for example, by the application of a cold bonding material, such as a high indium type solder, to increase the thickness of the ribbon 58. FIG. 16 shows an example of a ribbon 58 including an expanded portion that is formed, for example, by the application of a heat bonding material, such as a solder, brazing or weld material, to increase the width, and/or thickness of the ribbon 58. FIG. 17 shows an example of a ribbon 58 including an expanded portion that is formed, for example, by the application of a heat bonding material, such as a solder, brazing or weld material, to increase the width, and/or thickness of the ribbon 58, wherein the heat bonding material includes a "tail" or "bump" of heat bonding material attached thereto. Such a tail or bump can be useful to spread the heat bonding material to other locations along the joint when later heated.

It should be understood that the widened portion 60 can take any of a variety of forms, sizes, and/or shapes, and can be formed in any of a broad variety of ways. The embodiments shown in FIGS. 8-17 and the above description are includes by way of example.

Figure 18:
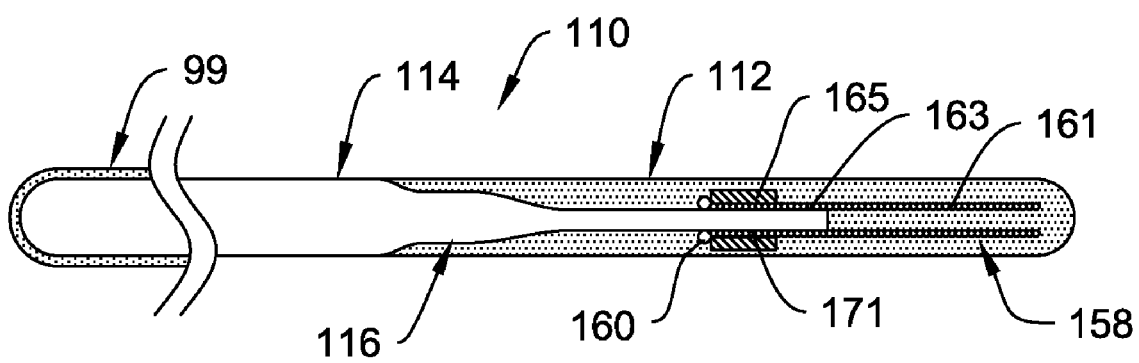
FIG. 18 is a partial schematic cross sectional view of another guidewire in accordance with one example embodiment.

Refer now to FIG. 18, which shows another alternative embodiment of a guidewire 110, similar to the guidewire 10 shown in FIG. 1, wherein like reference numbers indicate similar structure. The guidewire includes a core wire 114 that can have a similar construction to the core wire 14 discussed above. Additionally, the guidewire can include an attachment member 165 that can have a similar construction to the attachment member 65 discussed above. However, in this embodiment, the attachment member 165 can be adapted to be disposed about at least a portion of the core member 114 such that the space or gap 171 created between the inner surface of the attachment member and the outer surface of the core wire can extend about the circumference of the core wire 114. Additionally, in this embodiment, the structure 158 coupled to the core wire 114 is a generally tubular structure 158, such as a coil, that extends around a portion of the core wire 114, and includes a portion thereof that is disposed within the space or gap 171. The tubular structure 158 can be an elongated structure having a longitudinal axis, and having a distal region 161 and a proximal region 163. The ribbon includes an outer surface including an outer perimeter. The tubular member 158 is coupled to the core member 114 adjacent the distal section 116, and extends distally of the distal end of the core wire 114. In the embodiment shown, the tubular structure 158 is a generally straight structure that overlaps with and is coupled to the distal section 116.

Similar to the embodiments described above, the tubular structure 158 includes a widened and/or expanded region or portion 160. In the embodiment shown the expanded portion 160 is disposed adjacent the proximal region 163 of the tubular structure 158, however, in other embodiments, the expanded portion 160 can be disposed at other locations along the length of the tubular structure 158. The expanded portion 160 can be a portion of the tubular structure 158 that includes at least one dimension along the outer perimeter thereof that is greater that the same dimension of other portions of the tubular structure 158. For example, the expanded portion 160 may include a width, thickness, height, diameter, radius, or other such dimension that is greater than the same dimension of an adjacent portion of the tubular structure 158. In another respect, the expanded or widened portion 160 of tubular structure 158 can include at least a part thereof that includes an outer surface that extends a further distance away from the central longitudinal axis of the tubular structure 158 than an adjacent portion of tubular structure 158. For example, the widened portion 160 may include a widening, a bend, a bifurcation, one or more twists, a head, or additional material or structure added thereto that created a dimensional change in the outer surface of the tubular structure 158. In the embodiment shown, the coiled tubular structure 158 includes one or more proximal coil windings that has a greater size that the remaining coil windings, thus creating a widened portion 160 on the proximal end of the tubular structure 158. As such, another portion of tubular structure 158, such as the distal region 161, may have an outer perimeter that is adapted and/or configured to fit within or extend through a space, such as space 171, of predetermined size and shape, while the widened and/or expanded portion 160 of tubular structure 158 can be adapted and/or configured such that it cannot fit within or extend through the same space.

The widened portion 160 can be adapted and/or configured to engage the attachment member 165 and/or the core member 114 and can be used in coupling the tubular member 158 to the core member 114 in a similar manner as discussed above with regard to the other embodiments.

For example, a portion of the tubular member 158 can be disposed within the lumen of the centering ring 165, and the centering ring 165 can be disposed at a desired location about a portion of the core member 114. The tubular member would extend within the space or gap 171 formed between the inner surface of the centering ring 165 and the outer surface of the core member 114. The tubular member 58 can then be slid, pulled, or otherwise moved in a distal direction, such that the widened portion 160 is moved toward the attachment member 165. Due to the dimensional difference of the widened portion 160 as compared to the space 171, the widened portion 160 cannot slide through the space 171, and therefore engages the attachment member 165. The widened portion 160 mechanically engages, for example frictionally and/or interlockingly engages, the centering ring 165 and/or core member 114, and can create a mechanical coupling or bond between the centering ring 165, the ribbon 158, and/or the core member 114 such that the three components can remain in a static position relative to one another. In some embodiments, a part of the widened portion 160 may be deformed such that it fits tightly within the space 171 between the inner surface of the attachment member 165 and the outer surface of the core member 114. In some embodiments, the coupling may be used as is, or in other embodiments, an additional attachment technique can thereafter be used to further connect one or more of the components together or to other structure, for example, as disclosed above in the other embodiments.

This embodiment also illustrates the use of a polymer tip construction in that rather than an outer coil member, such as coil member 12, a polymer sleeve 112 is used. However, it should be understood that a coil member, such as coil member 12, may be used in this construction, or a polymer tip construction, such as polymer sleeve 112, may be used in the other embodiments disclosed herein. It should be understood that in some other embodiments, different tip configurations can be used. For example, some embodiments can include a combination of a flexible coil tip and/or polymer jacket tip. Some examples of additional components and tip constructions are disclosed in U.S. Pat. Nos. 6,918,882, 7,074,197 and 7,182,735; and U.S. Patent Publication No. 2004/0167441, all of which are incorporated herein by reference.

Additionally, in some embodiments, a coating, for example a lubricious (e.g., hydrophilic) or other type of coating may be applied over portions or all of the medical devices or structures discussed above. For example, such a coating may be applied over portions or all of the guidewires 10 and/or 110, including, for example, guidewire regions 16/18, the coil 12 or sleeve 112, the distal tip 49, or other portions of the guidewires 10 and 110. Hydrophobic coatings such as fluoropolymers, silicones, and the like provide a dry lubricity which improves guide wire handling and device exchanges. Lubricious coatings improve steerability and improve lesion crossing capability. Suitable lubricious polymers are well known in the art and may include hydrophilic polymers such as, polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the more distal portion of the guidewire is coated with a hydrophilic polymer as discussed above, and the more proximal portions is coated with a fluoropolymer, such as polytetrafluroethylene (PTFE). In the embodiments shown, a coating 99 such as a PTFE coating, is disposed over a proximal portion of the guidewires.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device comprising:
   an elongated core member having a proximal end and a distal end, and defining an outer surface;
   an elongated structure extending distally of the distal end of the elongated core member and including a first portion and a second expanded portion, wherein the first portion is distal the second expanded portion;
   a non-coiled attachment member disposed about a portion of the elongated core member and a part of the first portion of the elongated structure, the attachment member defining a lumen and having an inner surface; and
   an outer member comprising at least one of an outer coil member or a polymer member disposed about at least a portion of the elongated core member, the second portion of the elongated structure, and the attachment member;
   the device made by advancing part of the first portion of the elongated structure distally through a space between the inner surface of the attachment member and the outer surface of the elongated core member until a first part of the second expanded portion of the elongated structure moves into mechanical engagement with the inner surface of the attachment member and the outer surface of the elongated core member such that part of the first portion is disposed within the space, the first part of the second expanded portion is disposed within the space to provide a mechanical coupling of the elongated structure between the attachment member and the elongated core member, and a second part of the second expanded portion of the elongated structure cannot fit within the space;
   wherein the second part of the second expanded portion of the elongated structure is disposed proximal of the attachment member.

2. The medical device of claim 1, wherein the elongated structure comprises a ribbon.

3. The medical device of claim 1, wherein the elongated structure comprises a tubular member.

4. The medical device of claim 1, wherein the attachment member comprises a tubular member.

5. The medical device of claim 1, wherein the attachment member comprises an annular ring.

6. The medical device of claim 1, wherein the second expanded portion comprises a portion of the elongated structure that includes at least one size dimension that is greater than a corresponding size dimension of the first portion of the elongated structure.

7. The medical device of claim 6, wherein the second expanded portion includes at least one of a width or thickness, that is greater than a width or thickness of the first portion.

8. The medical device of claim 1, wherein the second expanded portion comprises an additional material added to the elongated structure.

9. The medical device of claim 8, wherein the additional material comprises a solder, braze, or weld material.

10. The medical device of claim 8, wherein the additional material comprises a cold welding material.

11. The medical device of claim 8, wherein the additional material comprises additional material added during construction of the elongated structure.

12. The medical device of claim 1, wherein the second expanded portion comprises a widening in the elongated structure.

13. The medical device of claim 1, wherein the second expanded portion comprises a curve, bend or twist in the elongated structure.

14. The medical device of claim 1, wherein the second expanded portion comprises a deformation in the elongated structure.

15. The medical device of claim 1, wherein the second expanded portion is defined by a change in the dimensions of the elongated structure.

16. The medical device of claim 1, wherein the second expanded portion comprises a bifurcation in the elongated structure.

17. The medical device of claim 1, wherein the medical device is a guidewire, and the core member is a solid core wire.

18. The medical device of claim 1, further including an additional attachment material connecting the attachment member to the elongated core and the elongated structure.

19. The medical device of claim 18, wherein the additional attachment material comprises welding, soldering, brazing, adhesive bonding, or expandable alloy material.

20. The medical device of claim 1, wherein the attachment member comprises a shape memory alloy, and the mechanical engagement connecting the attachment member to the elongated core and the elongated structure comprises using a shape memory effect to connect the attachment member to the elongated shaft and the elongated structure.

21. A medical device comprising:
an elongated core member having a proximal end and a distal end, and defining an outer surface;
an elongated structure extending distally of the distal end and having a first portion and a deformable second portion, wherein the first portion has a first dimension, the second portion has a second corresponding dimension that is greater than the first dimension, and the first portion is distal the second portion;
a non-coiled attachment member disposed about a portion of the elongated core member and a part of the first portion of the elongated structure, the attachment member defining a lumen and having an inner surface; and
an outer member comprising at least one of an outer coil member or a polymer member disposed about at least a portion of the elongated core member, the second portion of the elongated structure, and the attachment member;
the device made by: disposing part of the first portion of the elongated structure within a space between the inner surface of the attachment member and the outer surface of the elongated core member and
moving, after part of the first portion is disposed within the space, the elongated structure in a distal direction such that a first part of the second portion of the elongated structure is moved toward the attachment member and disposed within the space in mechanical engagement with the inner surface of the attachment member and the outer surface of the elongated core member to provide a friction fit of the first part of the second portion of the elongated structure between the attachment member and the elongated core member, and a second part of the second portion of the elongated structure cannot fit within the space;
wherein the second part of the second portion of the elongated structure is not in contact with the inner surface of the attachment member and the outer surface of the elongated core member.

22. A medical device comprising:
an elongated core member having a proximal end and a distal end, and defining an outer surface;
an elongated structure extending distally of the distal end and including a first portion having a first configuration, and a pre-formed second portion having a second configuration different from the first configuration, wherein a cross-sectional area of at least part of the second portion is greater than a cross-sectional area of the first portion, and wherein the first portion is distal the second portion;
a non-coiled attachment member disposed at a desired location about a portion of the elongated core member and a part of the first portion of the elongated structure, the attachment member defining a lumen and having an inner surface; and
an outer member comprising at least one of an outer coil member or a polymer member disposed about at least a portion of the elongated core member, the second portion of the elongated structure, and the attachment member;
the device made by: disposing part of the first portion of the elongated structure within a space between the inner surface of the attachment member and the outer surface of the elongated core member such that the second portion remains proximal of the attachment member during initial positioning of the attachment member at the desired location and
after initial positioning, advancing the elongated structure in a distal direction to move a first part of the second portion of the elongated structure from proximal of the attachment member to within the space and into mechanical engagement with the inner surface of the attachment member and the outer surface of the elongated core member to provide a mechanical coupling of the elongated structure between the attachment member and the elongated core member, and wherein a second part of the second portion of the elongated structure cannot fit within the space;
wherein the second part of the second portion of the elongated structure is disposed proximal of the attachment member.

23. A medical device having a proximal end and a distal tip, the medical device comprising:
an elongated core member having a first end and a second end, and defining an outer surface;
a unitary elongated structure formed of a single material extending between the elongated core member and the distal tip and having a length and a longitudinal axis along the length thereof, the unitary elongated structure including a first portion defining a first outer perimeter relative to the longitudinal axis, and a second expanded portion defining a second outer perimeter relative to the longitudinal axis, wherein the outer perimeter of the second expanded portion includes at least a part thereof that extends further from the longitudinal axis than any portion of the outer perimeter of the first portion, and wherein the first portion is distal the second expanded portion;
a non-coiled attachment member disposed about a portion of the elongated core member and a part of the first portion of the unitary elongated structure, the attachment member defining a lumen and having an inner surface; and
an outer member comprising at least one of an outer coil member or a polymer member disposed about at least a portion of the elongated core member, the second expanded portion of the unitary elongated structure, and the attachment member;
wherein part of the first portion of the unitary elongated structure is disposed within a space between the inner surface of the attachment member and the outer surface of the elongated core member;
wherein a first part of the second expanded portion of the unitary elongated structure is in mechanical engagement with the inner surface of the attachment member and the outer surface of the elongated core member such that the first part of the second expanded portion is disposed within the space to provide a mechanical coupling of the unitary elongated structure between the attachment member and the elongated core member, and a second part of the second expanded portion of the unitary elongated structure cannot fit within the space;

wherein the unitary elongated structure extends distally of the elongated core member and the attachment member.

24. A medical device having a proximal end and a distal tip, the medical device comprising:
- an elongated core member having a first end and a second end, and defining an outer surface;
- an elongated structure extending from the elongated core member toward the distal tip and having a first portion having a first outer perimeter and a deformable second portion having a second outer perimeter different from the first outer perimeter, wherein the first portion is distal the second portion;
- a non-coiled attachment member disposed about a portion of the elongated core member and a part of the first portion of the elongated structure, the attachment member defining a lumen and having an inner surface; and
- an outer member comprising at least one of an outer coil member or a polymer member disposed about at least a portion of the elongated core member, the second portion of the elongated structure, and the attachment member;
- the device made by: disposing part of the first portion of the elongated structure within a space between the inner surface of the attachment member and the outer surface of the elongated core member with the second portion positioned proximally of the attachment member and
- advancing the elongated structure within the space by a distally-directed force applied to the elongated structure such that a first part of the second portion moves into contact with both the attachment member and the elongated core member, is deformed to fit tightly within the space, and becomes frictionally engaged with the inner surface of the attachment member and the outer surface of the elongated core member to provide a mechanical coupling of the elongated structure between the attachment member and the elongated core member, and a second part of the second portion of the elongated structure cannot fit within the space;

wherein the second part of the second portion of the elongated structure is not in contact with the inner surface of the attachment member and the outer surface of the elongated core member.

* * * * *